United States Patent [19]
Oftring et al.

[11] Patent Number: 6,034,257
[45] Date of Patent: Mar. 7, 2000

[54] METHOD FOR SEPARATING GLYCERIN FROM REACTION MIXTURES CONTAINING GLYCERIN AND FATTY ACID AMIDES, ALKOXYLATED AMIDES OBTAINED THEREFROM AND THE USE THEREOF

[75] Inventors: Alfred Oftring, Bad Dürkheim; Günter Oetter, Frankenthal; Richard Baur, Mutterstadt; Oliver Borzyk, Speyer; Bernd Burkhart, Mutterstadt; Christian Ott, Speyer; Martin aus dem Kahmen, Ludwigshafen, all of Germany

[73] Assignee: BASF Aktiengesellschaft, Ludwigshafen, Germany

[21] Appl. No.: 09/308,669

[22] PCT Filed: Dec. 2, 1997

[86] PCT No.: PCT/EP97/06750

§ 371 Date: Jun. 3, 1999

§ 102(e) Date: Jun. 3, 1999

[87] PCT Pub. No.: WO98/24758

PCT Pub. Date: Jun. 11, 1998

[30] Foreign Application Priority Data

Dec. 3, 1996 [DE] Germany .......................... 196 50 107
Dec. 3, 1996 [DE] Germany .......................... 196 50 151

[51] Int. Cl.[7] ................................................ C07C 231/00
[52] U.S. Cl. ................................ 554/69; 554/68; 554/70
[58] Field of Search ................................ 554/68, 69, 70

[56] References Cited

FOREIGN PATENT DOCUMENTS 40 19 089  1/1991  Germany .

OTHER PUBLICATIONS

J.K. Weil, et al., Journal of the American Oil Chemists' Society, pp. 674–677, "Tallow Alkanolamides: Preparation and Effect on Surfactant Solutions[1]," 1971.

Chemical Abstract, AN 48459U–DE, JP 7326921, Aug. 17, 1973.
Chemical Abstract, AN 61525U–B, JP 7332081, Oct. 04, 1973.
Chemical Abstract, AN 93–406545/51, DE 4218837, Dec. 16, 1993.
Chemical Abstract, AN 96–300543/30, WO 96/18608–A1, Jun. 20, 1996.

*Primary Examiner*—Deborah Carr
*Attorney, Agent, or Firm*—Oblon, Spivak, McClelland, Maier & Neustadt, P.C.

[57] ABSTRACT

In a process for preparing an alkoxylated amide of the formula (I)

$$R^1\text{—CO—NR}^2\text{—CHR}^3\text{—CHR}^4\text{—O—(CHR}^5\text{—CHR}^6\text{—O)}_n\text{—H} \quad (I)$$

(1) glycerides of the fatty acids, specified later on, of the formula (II):

$$R^1\text{—COOH} \quad (II)$$

are reached with amines of the formula (III)

$$HNR^2R^7 \quad (III)$$

to give amides of the formula (IV)

$$R^1\text{—CO—NR}^2\text{—R}^7 \quad (IV)$$

and glycerol, (2) then the glycerol which has been formed is separated off by adding of aqueous acid solution to the reaction mixture until it has a pH in the range 1–7, in order to bring about phase separation into a glycerol-containing aqueous phase and an organic phase containing amides of the formula (IV), and separating off the aqueous phase, and (3) subsequently the amide of the formula (IV) is reacted with ethylene oxide and/or propylene oxide and/or butylene oxide to give alkoxylated amides of the formula (I).

13 Claims, No Drawings

METHOD FOR SEPARATING GLYCERIN FROM REACTION MIXTURES CONTAINING GLYCERIN AND FATTY ACID AMIDES, ALKOXYLATED AMIDES OBTAINED THEREFROM AND THE USE THEREOF

This application is a 371 of PCT/EP97/00006 filed Dec. 2, 1997.

The invention relates to alkoxylated amides, processes for preparing such tertiary amides, their use, especially in detergents, cleaning products and bodycare compositions, and compositions comprising them.

The invention relates also to processes for separating glycerol from reaction mixtures containing glycerol and fatty acid amides, the reaction mixture preferably originating from the above reaction of fatty acid glycerides with amines to produce tertiary amides.

A large number of fatty acid amides and their ethoxylates are known, as is their suitability as surface-active substances. J. H. Weil, N. Pares, W. R. Nobel, F. D. Smith, A. J. Stirton in J. Am. Oil Chem. Soc., 1971, pages 674 to 677 describe fatty acid alkanolamides. Those described in particular are N-methylethanolamides of pelargonic, lauric, palmitic, stearic and oleic acid. Also described are ethylene oxide and propylene oxide adducts of diethanolamides of palmitic, stearic and pelargonic acid. The compounds can be used as constituents of detergent formulations and cosmetics. The compounds were prepared from the methyl esters of the corresponding acids. Ethylene oxide adducts of N-methylethanolamides are not described.

DE-A1-42 16 316 describes tertiary amides and their use as low-foaming wetting agents in the textile industry. The tertiary amides are derived from fatty acids and N-alkylethanolamines having $C_{3-6}$-alkyl radicals. Mention is made in particular of amides of isononanoic acid and N-butylethanolamine, N-hexylethanolamine, N-hexylisopropanolamine and N-(2-ethylhexyl) ethanolamine, which are ethoxylated.

The compounds are used as low-foaming wetting agents in the preparation and finishing of textiles, especially in the dyeshop in the preparation, pretreatment and dyeing of raw product. Tertiary amides of N-methylamines or N-ethylamines are not described. To prepare the tertiary amides, the carboxylic acids are reacted with the amines and are then ethoxylated.

A number of process for preparing fatty acid amides are known. The reaction of fatty acid glycerides with amines to give fatty acid amides and glycerol is known. In many cases the glycerol formed then remains in the product mixture. Processes for separating glycerol from the reaction mixture are also known. JP-A-7332081 describes a process for preparing fatty acid amides in which a natural oil and an amine compound are reacted. For example, linseed oil is reacted with cyclohexylamine, and the resulting solution is poured into ice-cold hydrochloric acid and subjected to extraction with ether. The etherial extract is washed with 5% HCl, 5% $Na_2CO_3$ and $H_2O$, dried over $Na_2SO_4$ and concentrated under reduced pressure. The residue is subjected to fractional distillation in order to give the desired fatty acid amide.

JP-A-7326921 describes a process for the aminolysis of glyceride fats and oils with amines. Glycerol is removed from the equilibrium by forming borate esters of boric acid or boric anhydride. Polymerized glycerol borates settle at the bottom of the reaction mixture.

DE-C-40 19 089 describes a process for direct recovery of fatty acid amides from crude fats and oils, wherein the latter are reacted with diaminoethane or diaminohexane. The reaction product is recrystallized from methanol.

DE-A42 18 837 describes a process for preparing N,N'-bisacylalkylenediamines with pure C chains. In this process, oils and ethylenediamine are reacted in the presence of p-toluenesulfonic acid as catalyst. The yellowish waxlike crude product obtained is then dispersed in hot water and filtered through a suction filter. The filtrate is a virtually nitrogen-free glycerol concentrate.

WO 96/18608 describes the synthesis of fatty acid N-alkylamides. The amides are prepared by reacting oils with amines. The crystalline fatty acid N-alkylamides are isolated either by filtration or by addition of hexane, in which case a hexane phase containing the fatty acid N-alkylamide is separated by decantation from a glycerol-containing phase.

In the above processes glycerol is either precipitated by the addition of expensive chemicals such as boric acid, or the fatty acid amide is separated from the glycerol phase with the aid of an organic solvent. The product must then again be isolated from the organic solvent. Processes in which the glycerol is simply washed out with hot water or filtered off result in products whose purity is unsatisfactory and which contain major amounts of residual glycerol.

It is one object of the present invention to provide alkoxylated amides having excellent properties as surface-active compounds, emulsifiers and, in particular, nonionic surfactants.

It is another object of the present invention to provide a process for preparing such tertiary amides, where the amides are obtained in high purity.

Another object of the present invention is to provide a process for separating glycerol from reaction mixtures containing glycerol and fatty acid amides, which is uncomplicated and cost-effective, avoids the drawbacks of the known processes and produces highly pure fatty acid amides.

We have found that these objects are achieved, in accordance with the invention, by providing alkoxylated amides of the formula (Ia)

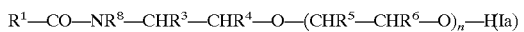

where $R^1$ is a linear or branched aliphatic $C_{5-25}$ radical containing 0–5 double bonds, $R^8$ is methyl or ethyl, $R^3$, $R^4$, $R^5$ and $R^6$ are hydrogen, or not more than one of $R^3$ and $R^4$ and not more than one of $R^5$ and $R^6$ are methyl or ethyl, and n is 1–100.

We have also found that the objects are achieved by a process for preparing alkoxylated amides of the formula (I)

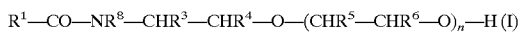

where $R^1$ is a linear or branched aliphatic $C_{5-25}$ radical containing 0–5 double bonds, $R^2$ is hydrogen or a linear or branched $C_{1-20}$ alkyl which may be interrupted by from 1 to 5 oxygens, $R^3$, $R^4$, $R^5$ and $R^6$ are hydrogens or not more than one of $R^3$ and $R^4$ and not more than one of $R^5$ and $R^6$ are methyl or ethyl, and n is 1–100, by (1) reacting glycerides of the fatty acids, specified later on, of the formula (II)

$$R^1\text{—COOH} \quad (II)$$

with amines of the formula (III)

$$HNR^2R^7 \quad (III)$$

where $R^7$ is hydrogen or —$CHR^3$—$CHR^4$—OH, in which not more than one of $R^2$ and $R^7$ is hydrogen, to give amides of the formula (IV)

$$R^1\text{—CO—}NR^2R^7 \quad (IV)$$

where $R^1$, $R^2$ and $R^7$ are as defined above, and glycerol, (2) then separating off the glycerol which has been formed, by adding aqueous acid solution to the reaction mixture until it has a pH in the range 1–7, in order to bring about phase separation into a glycerol-containing aqueous phase and an organic phase containing amides of the formula (IV), and separating off the aqueous phase, and (3) subsequently reacting the amide of the formula (IV) with ethylene oxide, propylene oxide and/or butylene oxide to give alkoxylated amides of the formula (I).

We have found that these objects are furthermore achieved by a process for separating glycerol from reaction mixtures comprising glycerol and fatty acid amides, wherein the reaction mixture, by its pH being set to a value in the range from 1 to 7 by the addition of aqueous acid solution, is caused to undergo phase separation into an aqueous phase comprising glycerol and an organic phase comprising fatty acid amides and the aqueous phase is separated off.

Of the alkoxylated amides of the formula (Ia) the invention prefers those in which $R^1$ is a linear or branched aliphatic $C_{5-25}$, preferably $C_{5-21}$, particularly preferably $C_{7-21}$, especially $C_{11-17}$ radical containing from 0 to 5, preferably from 0 to 3, especially from 0 to 2 double bonds. Thus it can be a linear or branched saturated alkyl radical or an unsaturated radical having from 1 to 5, preferably from 1 to 3, especially 1 or 2 double bonds. $R^1$ preferably derives from a natural fatty acid. Oils containing these natural fatty acids, which can be employed with preference in accordance with the invention, are tallow oil, palm kernel oil, palm oil, sunflower oil, groundnut oil, rapeseed oil, soya oil, coconut oil or other types of natural oil.

$R^8$ in (Ia) is methyl or ethyl, preferably methyl. In (I) it is called $R^2$ and can be hydrogen or linear or branched $C_{1-20}$ alkyl, preferably hydrogen or $C_{1-12}$, especially $C_{1-6}$, alkyl which may be interrupted by from 1 to 5, preferably 1, oxygen atom(s).

$R^3$, $R^4$, $R^5$ and $R^6$ are hydrogens or not more than one of $R^3$ and $R^4$ and not more than one of $R^5$ and $R^6$ are methyl or ethyl. In particular, not more than one of $R^3$ and $R^4$ and not more than one of $R^5$ and $R^6$ are methyl. With particular preference, all of $R^3$, $R^4$, $R^5$ and $R^6$ are hydrogens.

n is from 1 to 100, preferably from 1 to 50, with particular preference from 1 to 20, in particular from 2 to 20, especially from 2 to 17.

Particularly preferred compounds are the reaction products of the acids present in rapeseed oil or coconut oil with methylamine, ethanolamine, N-methylethanolamine or N-ethylethanolamine having from about 1 to 12, especially 3 to 9, ethylene oxide units.

The novel alkoxylated amides and other tertiary amides can be prepared by the above process, wherein first of all glycerides, preferably triglycerides, derived from the fatty acids, specified below, of the formula (II)

$$R^1\text{—COOH} \quad (II)$$

are reacted with amines of the formula (III)

$$HNR^2R^7 \quad (III)$$

to give amides of the formula (IV)

$$R^1\text{—CO—}NR^2R^7.$$

In these formulae, $R^1$ is as defined above. $R^2$ is linear or branched $C_{1-20}$, often $C_{1-12}$, preferably $C_{1-6}$, particularly preferably $C_{1-2}$ alkyl, especially methyl. $R^2$ can be interrupted by from 1 to 5, preferably 1, oxygen(s).

$R^3$, $R^4$, $R^5$ and $R^6$ are as defined above. $R^7$ is hydrogen or a radical —$CHR^3$—$CHR^4$—OH with $R^3$ and $R^4$ being as defined above and not more than one of $R^3$ and $R^7$ being hydrogen.

Particularly preferred triglycerides are the natural oils listed above.

The reaction of the fatty acid of the formula (II) with the amine of the formula (III) in process stage (1) takes place preferably in the presence of a basic catalyst, which can be any customary, suitable basic catalyst, examples being alcoholates, especially alkali metal alcoholates of $C_{1-4}$ alkanols, for example sodium methanolate, sodium methanolate, sodium isopropylate or potassium tert-butylate; hydrides, for example sodium hydride, sodium borohydride or lithium aluminum hydride; alkali metal or alkaline earth metal hydroxides, for example sodium hydroxide, potassium hydroxide, lithium hydroxide or calcium hydroxide; alkali metal carbonates, for example sodium carbonate, potassium carbonate or lithium carbonate; salt like amides, for example lithium diisopropylamide; lithium organyls, such as alkyllithium compounds, for example n-butyllithium or methyllithium or phenyllithium. It is preferred to employ an alkali metal methanolate, especially $NaOCH_3$. The catalyst is employed in an amount of from 0.1 to 50 mol %, preferably from 1 to 30 mol % and, in particular, from 5 to 25 mol %, based on the glyceride. The preferred reaction temperature is from 20 to 200° C., preferably from 50 to 150° C. and, in particular, from 60 to 100° C. At this preferred level the solvent in which the catalyst, especially $NaOCH_3$, can be charged, especially methanol, is distilled off. The reaction of oil and lower alkylamine, if the latter is a gas, is preferably conducted in an autoclave. When using amines which are liquid at room temperature, such as N-alkylethanolamines, the reaction can be conducted in a normal reaction vessel at ambient pressure, by charging the amine and the catalyst to the vessel and adding the oil.

The time for the reaction is preferably from 0.1 to 10 hours, with particular preference from 1 to 7 hours and, in particular, from 1.0 to 3 hours. The pressure in the reaction system when using liquid amines is preferably ambient pressure and when using gaseous amines is preferably the autogenous pressure, i.e. that pressure which is established in the reaction system for a given amount of amine.

The reaction in process stage (2) leads to the above-described amines and glycerol. Since the glycerol interferes with subsequent reaction steps, it is separated off before the reaction continues. The separation process used for this is described in the following.

It was found, according to the invention, that phase separation of the reaction mixture can be achieved by the addition of aqueous acid solution to the reaction mixture. To this end, the pH of the reaction mixture is brought to within a range of from 1 to 7, preferably from 2 to 5, in particular from 3 to 4. The aqueous acid solution used for this purpose may have been prepared from any acid which under the conditions of phase separation does not react with the fatty acid amides or glycerol. The acid should not act as an oxidant. In particular, no glycerol esters should be formed with the acid. Suitable acids for example contain N, S and/or P as heteroatoms. Examples of sulfur-containing acids are sulfuric acid and sulfonic acids such as methanesulfonic acid or toluenesulfonic acid. Examples of phosphorus-containing acids are phosphoric acid, phosphorous acid. It is also possible to use hydrohalic acids such as HCl. It is further possible to use acids such as alkanoic acids, e.g. acetic acid, or hydroxycarboxylic acids such as citric acid, lactic acid or tartaric acid. Examples of preferred inorganic acids are hydrochloric acids or phosphoric acid. Preferred organic acids are formic acid, acetic acid and further aliphatic and aromatic carboxylic acids. Preference is given to the use of cost-effective acids available industrially, in particular acetic acid or hydrochloric acid, especially hydrochloric acid. The hydrochloric acid solution used may have any concentration which allows, upon addition of suitable amounts, to obtain the desired pH values in the reaction mixture.

After the addition of aqueous acid solution a two-phase system is formed with a glycerol-containing aqueous phase and an organic phase containing fatty acid amides. The aqueous phase is then separated from the organic phase by suitable methods, only very small amounts of glycerol or none at all remaining in the organic phase. Generally it is possible to lower the glycerol content in the fatty acid amides obtainable from the organic phase to less than 0.1 wt %.

Moreover, the glycerol can again be isolated from the aqueous phase and can therefore be used as a valuable product in further reactions. The closed recycle loop thus made possible means that the process for preparing fatty acid amides is environment-friendly.

The phase separation, i.e. the addition of acid and the separation of the phases takes place at a suitable temperature, preferably at less than 100° C.

According to one embodiment of the invention phase separation may be promoted by the reaction mixture additionally being admixed with an organic phase separation medium. The organic phase separation medium used may comprise any suitable organic compound, in particular aliphatic aldehydes and ketones, for example 2-butanone. In the process, the organic phase separation medium forms an organic phase containing the fatty acid amides, which separates more readily from the glycerol-containing aqueous phase.

Where possible, the invention does not involve the addition of a further organic phase separation medium, making the process less complicated, since after phase separation the organic phase separation medium does not have to be separated from the desired fatty acid amides.

As a rule, the reaction mixture containing glycerol and fatty acid amides originates from a reaction of fatty acid glycerides with amines, fatty acid triglycerides being a preferred starting material. Suitable fatty acids in this context are all naturally occurring or synthetic fatty acids. Examples of suitable fatty acid radicals are radicals $R^1$—CO—, where $R^1$ is a linear or branched aliphatic $C_{5-25}$ radical containing from 0 to 5 double bonds. Preferred are $C_{7-21}$, in particular $C_{11-17}$ radicals which preferably contain from 0 to 3, in particular from 0 to 2 double bonds. Examples of suitable triglycerides are, in particular, tallow oil, palm nut oil, palm oil, sunflower oil, peanut oil, rape oil, soybean oil, coconut oil and similar types of oil.

The amine radical used in the fatty acid amide is preferably a radical which derives from a N—$C_{1-20}$-, preferably N—$C_{1-6}$-, particularly preferably N—$C_{1-3}$-alkylamine or a corresponding -alkylethanolamine, the ethanol radical possibly being substituted by methyl or ethyl. The alkyl may be linear or branched and be interrupted by from 1 to 5 oxygen atoms.

The invention therefore also relates to a process for preparing fatty acid amides by reacting fatty acid glycerides, in particular fatty acid triglycerides with amines, the reaction mixture obtained after the reaction being treated or worked up as described above. The reaction in this context preferably takes place in the presence of a basic catalyst as described above. The fatty acid amides thus obtained according to the invention, which are largely or preferably almost completely or entirely free from glycerol, may be used to great advantage in a subsequent reaction with alkylene oxides such as ethylene oxide, propylene oxide or butylene oxide. Owing to the very low glycerol content or to the freedom from glycerol, considerably more uniform and cleaner alkoxylation of the amides is possible, in particular since alkoxylation of the glycerol does not take place. A subsequent alkoxylation therefore gives rise to very uniform and pure products.

The N-alkyl-N-ethanolamides in particular can be alkoxylated very uniformly, since the alkoxylation takes place only on the ethanol group. Side reactions such as the double alkoxylation on the amide nitrogen as occurs in the case of primary amides are avoided.

The separation process according to the present invention is cost-effective and environment-friendly, allows native fats and oils to be employed without the use of further solvents and produce very small amounts of by-products. The alkoxylation products which can be prepared from the fatty acid amides can advantageously be used, in particular, as nonionic surfactants. In the following this process step is described specifically relating to process step (2).

In this step, practiced in stage (2) of the process, glycerol formed in the amide-producing reaction is removed by adding aqueous acid solution to the reaction mixture to give it a pH in the range from 1–7, preferably 2–5, especially 3–4, in order to effect phase separation into a glycerol-containing aqueous phase and an organic phase containing amides of the formula (IV), and separating off the aqueous phase. Under the conditions of phase separation, the acid reacts neither with the amides nor with glycerol. In particular, no glycerol esters are formed. Appropriate acids and the further process are described above. Following the removal of the aqueous phase, the organic phase can also be washed one or more times with water. The organic phase can be dried by concentration under reduced pressure, for example the subatmospheric pressure produced by an oil pump. Any water or solvent still present in the organic phase can also be removed by other methods, for example using siccatives. Appropriate procedures are familiar to the skilled worker.

In a subsequent stage (3), the amide, which is preferably being dried, is reacted with ethylene oxide and/or propylene oxide and/or butylene oxide to form alkoxylated amides of the formula (I). This reaction can be carried out with mixtures of alkylene oxides, possibly leading to random incorporation of the alkylene oxides. Stepwise reaction with different alkylene oxides is also possible, in which case blocks or controlled sequences of the alkylene oxides are incorporated into the compounds. In this context, the reaction takes place preferably in an autoclave, and can be conducted in the presence of an appropriate basic catalyst which may be the same as the catalyst used in the first stage. Otherwise, suitable catalysts are hydrophobicized hydrotalcites, strontium acetylacetonate or barium acetylacetonate, lipases, aluminates, phosphates, or tertiary amines, for example triethylamine, and also heterogenous (e.g. $AlCl_3$) and homogeneous (e.g. $BF_3Et_2O$) Lewis acids. It is preferred ta use $NaOCH_3$, as it is or as a solution in methanol. In this case, the amide of the formula (IV) is charged to the autoclave, the catalyst is introduced, and, if desired, drying is carried out again at 60–180° C., preferably 80–140° C., under a pressure of 5–500 mbar, preferably from 10 to 25 mbar, by stripping off solvents that are present. Reaction with ethylene oxide or propylene oxide takes place preferably at from 60–180° C., especially 80–140° C., under a maximum pressure of preferably 10 bar, particularly preferably 5 bar, especially 4 bar. The progress of this reaction can be monitored by way of the reduction in pressure. Following the reaction, the reaction mixture is cooled, preferably to 60–100° C., in particular about 80° C., and devolatilized under reduced pressure.

The process according to the invention, especially the substantially complete separation of the glycerol in the second stage, makes it possible to achieve uniform alkoxylation of the amides of the formula (IV). The resulting alkoxylation products are substantially purer and more uniform than those obtained by known processes. The uniformity of the product has advantageous implications for its surfactant properties. As a result of the use of N-alkylamides or N-alkanolamines, alkoxylation at only one position of the molecule, the hydrogen attached to nitrogen in the case where alkylamines are used or the hydroxyl group in the case where N-(alkyl)alkanolamines are used, is preferred. The use of the specific amines or amides of the formula (IV) leads in turn to highly uniform alkoxylation products. The invention also relates to the alkoxylated amides which can be prepared by the above process.

It is preferred therein to use N-(alkyl)ethanolamines or the corresponding amides, since under these conditions alkoxylation is more uniform and more complete than when alkylamines or corresponding amides are used.

The alkoxylated amides of the formulae (I) and (Ia) according to the invention can be used, in accordance with the invention, as surface-active compounds, as nonionic surfactants or as emulsifiers. In this function they can be used in detergents, cleaning products or bodycare compositions, in electroplating, in the photographic industry, in petroleum extraction, in the pharmaceutical industry, in plant nutrition and in crop protection formulations, and also in the production of emulsions, pigment dispersions and polymer dispersions. Other suitable fields of use of the novel compounds are fiber lubricants and chain lubricants, and also treatment baths for textiles and fibers.

The novel compounds (I) and (Ia) can be used in the production and processing of textiles and plastics, in paints and printing inks, in mold release agents, in metal-working or in the paper or leather industry. In these applications they are used as advantageous surfactants, having enhanced activity and enhanced hydrolysis resistance relative to known surfactants. In the production and processing of textiles they are ideally employed in fiber pretreatment compositions, in the production of rayon fiber, in spin finishes and textile melts, in dyeing assistants, in finishes generally, in hydrophobicizing compositions, in printing assistants, in antistats and in flocculants and coating compositions.

In addition, compounds according to the invention are employed in paints and printing inks and also in both aqueous and nonaqueous systems. In nonaqueous systems they serve principally as dispersing auxiliaries, antisettling agents or leveling assistants. In addition, the compounds of the invention enable high-solids systems to be produced. In aqueous systems their function, in addition to stabilizing the polymer dispersion-based binders produced by emulsion addition polymerization or emulsion polycondensation, is also as an aid to dispersing the organic and inorganic pigments that are often employed. Furthermore, they improve the adhesion properties of these coating compositions.

The compounds of the invention are employed, moreover, in mold release agents as used, for instance, in the plastics processing industry. Their function here is to separate the casting from the mold (as also, for example, in mold oils for concrete formwork). Aqueous emulsions are usually employed for this purpose.

In the production and processing of polymers the compounds according to the invention are preferably employed in the production of polymer dispersions, in the preparation of bead polymers, in the preparation of foams, as surface-active mold release agents, for producing microcapsules, for improving the adhesion between fillers and plastics, in polymer dispersion additives for achieving particular effects, such as foamability, filler compatibility or wetting power, as emulsifiers for nonaqueous systems, in coloring plastics, and in the antistatic finishing of plastics.

The compounds of the invention can be employed, moreover, in metalworking, especially in cooling lubricants, hardening oils, hydraulic oil emulsions, polishing pastes, mold release agents, drawing oils, pickling compositions, metal cleaners and metal driers.

The compounds of the invention can also be employed in the paper and leather industries.

The compounds of the invention are preferably used in detergents, cleaning products and bodycare compositions. The invention therefore also relates to detergents, cleaning products and bodycare compositions which comprise, based on the overall weight of the composition, 0.1–50% by weight of at least one alkoxylated amide of the formula (I) or (Ia). The detergent or cleaning product can be used in accordance with the invention for cleaning textiles, for manual or mechanical dishwashing, and in technical cleaning product formulations.

The customary constituents of the novel detergents include builders, surfactants, bleaches, enzymes and other ingredients, as described below.

Builders

Inorganic builders (A) suitable for combination with the novel surfactants are, in particular, crystalline or amorphous alumosilicates having ion exchanges properties, especially zeolites. Various types of zeolites are suitable, especially zeolites A, X, B, P, MAP and HS in their Na form or in forms in which some of the Na has been exchanged for other cations, such as Li, K, Ca, Mg or ammonium. Suitable zeolites are described, for example, in EP-A 0 038 591, EP-A 0 021 491, EP-A 0 087 035, U.S. Pat. No. 4,604,224, GB-A 2 013 259, EP-A 0 522 726, EP-A 0 384 070 and WO-A 94/24251.

Suitable crystalline silicates (A), for example, are disilicates or phyllosilicates, for example SKS-6 (manufacturer: Hoechst). The silicates can be employed in the form of their alkali metal, alkaline earth metal or ammonium salts, preferably as Na, Li and Mg silicates.

Amorphous silicates, for example sodium metasilicate, which has a polymeric structure, or Britesil® H20 (manufacturer: Akzo), can likewise be used.

Suitable inorganic builder substances based on carbonate are carbonates and hydrogen carbonates. These can be employed in the form of their alkali metal alkaline earth metal or ammonium salts. Preference is given to employing Na, Li and Mg carbonates and hydrogen carbonates, especially sodium carbonate and/or sodium hydrogen carbonate.

Customary phosphates as inorganic builders are polyphosphates, for example pentasodium triphosphate.

These components (A) can be employed individually or in mixtures with one another. Of particular interest as inorganic builder component is a mixture of alumo-silicates and carbonates, especially of zeolites, especially zeolite A, and alkali metal carbonates, especially sodium carbonate, in a weight ratio of from 98:2 to 20:80, in particular from 85:15 to 40:60. Other components (A) may also be present in addition to this mixture.

In a preferred embodiment, the novel textile detergent formulation contains from 0.1 to 20% by weight, in particular from 1 to 12 percent by weight, of organic cobuilders (B) in the form of low molecular mass, oligomeric or polymeric carboxylic acids, especially polycarboxylic acids, or phosphonic acids or salts thereof, especially Na or K salts.

Examples of suitable low molecular mass carboxylic acids or phosphonic acids for (B) are:

$C_4$- to $C_{20}$ di-, -tri- and -tetracarboxylic acids, for example succinic, propanetricarboxylic, butanetetracarboxylic and cyclopentanetetracarboxylic acid and alkyl- and alkenylsuccinic acids having $C_2$- to $C_{16}$-alkyl and, respectively, -alkenyl radicals;

$C_4$- to $C_{20}$-hydroxycarboxylic acids, for example malic, tartaric, gluconic, glutaric, citric and lactobionic acid and sucrose mono-, -di- and tricarboxylic acid; aminopolycarboxylic acids, for example nitrilotriacetic acid, β-alaninediacetic acid, ethylenediaminetetraacetic, serinediacetic, isoserinediacetic and methylglycinediacetic acid and alkylethylenediamine triacetates; salts of phosphonic acids, for example hydroxyethanediphosphonic acid.

Examples of suitable oligomeric or polymeric carboxylic acids (B) are:

oligomaleic acids, as described for example in EP-A 451 508 and EP-A 396 303; co- and terpolymers of unsaturated $C_4$–$C_8$ dicarboxylic acids, possible copolymerized monomers being monoethylenically unsaturated monomers from the group (i) in amounts of up to 95% by weight, from the group (ii) in amounts of up to 60% by weight, and from the group (iii) in amounts of up to 20% by weight.

Examples of unsaturated $C_4$–$C_8$ dicarboxylic acids in this context are maleic, fumaric, itaconic and citraconic acid. Preference is given to maleic acid.

The group (i) comprises monoethylenically unsaturated $C_3$–$C_8$ monocarboxylic acids, for example acrylic, methacrylic, crotonic and vinylacetic acid. From the group (i), preference is given to using acrylic and methacrylic acid.

The group (ii) comprises monoethylenically unsaturated $C_2$–$C_{22}$ olefeins, $C_1$—$C_8$-alkyl vinyl ethers, styrene, vinyl esters of $C_1$—$C_8$ carboxylic acids, (meth)acrylamide and vinylpyrrolidone. From the group (ii), preference is given to employing $C_2$–$C_6$ olefins, $C_1$–$C_4$-alkyl vinyl ethers, vinyl acetate and vinyl propionate.

The group (iii) comprises (meth)acrylic esters of $C_1$ to $C_8$ alcohols, (meth)acrylonitrile, (meth)acrylamides of $C_1$ to $C_8$ amines, N-vinylformamide and vinylimidazole.

If the polymers of group (ii) contain vinyl esters incorporated by polymerization, they may also, in whole or in part, have been hydrolyzed to give vinyl alcohol structural units. Examples of suitable co- and terpolymers are known from U.S. Pat. No. 3,887,806 and DE-A 43 13 909.

Suitable copolymers of dicarboxylic acids for component (B) are preferably:

copolymers of maleic acid and acrylic acid in a weight ratio of from 100:90 to 95:5, preferably from 30:70 to 90:10, having molar masses from 100,000 to 150,000;

terpolymers of maleic acid, acrylic acid and a vinyl ester of a $C_1$–$C_3$ carboxylic acid in a weight ratio of from 10(maleic acid):90 (acrylic acid+vinyl ester) to 95(maleic acid):10 (acrylic acid+vinyl ester), the weight ratio of acrylic acid to the vinyl ester varying in the range from 30:70 to 70:30;

copolymers of maleic acid with $C_2$–$C_8$ olefins in a molar ratio of from 40:60 to 80:20, particular preference being given to copolymers of maleic acid with ethylene, propylene or isobutene in a molar ratio of 50:50.

Graft polymers of unsaturated carboxylic acids on low molecular mass carbohydrates or hydrogenated carbohydrates—cf U.S. Pat. No. 5,227,446, DE-A 44 15 623 and DE-A 43 13 909—are likewise suitable as component (B).

Examples of suitable unsaturated carboxylic acids in this context are maleic, fumaric, itaconic, citraconic, acrylic, methacrylic, crotonic and vinyl acetic acid and also mixtures of acrylic and maleic acid, which are grafted on in amounts of from 40 to 95% by weight, based on the component to be grafted.

For modification it is additionally possible for up to 30% by weight, based on the component to be grafted, of further monoethylenically unsaturated monomers to be present in copolymerized form. Suitable modifying monomers are the abovementioned monomers of groups (ii) and (iii).

Suitable as graft base are degraded polysaccharides, for example acidic or enzymatically degraded starches, inulins or cellulose, protein hydrolyzates and reduced (hydrogenated or reductively aminated) degraded polysaccharides, for example mannitol, sorbitol, aminosorbitol and N-alkylglucamine, and also polyalkylene glycols having molar masses of up to $M_w$=5000, for example polyethylene glycols, ethylene oxide-propylene oxide or ethylene oxide-butylene oxide or ethylene oxide-propylene oxide-butylene oxide block copolymers and alkoxylated mono- or polyhydric $C_1$ to $C_{22}$ alcohols; cf U.S. Pat. No. 5,756,456.

From this group, preference is given to the use of grafted, degraded or degraded, reduced starches and grafted polyethylene oxides, with from 20 to 80% by weight of monomer, based on the graft component, being employed in the graft polymerization. Grafting is preferably conducted using a mixture of maleic acid and acrylic acid in a weight ratio of from 90:10 to 10:90.

Polyglyoxylic acids suitable as component (B) are described, for example, in EP-B 001 004, U.S. Pat. No. 5,399,286, DE-A 41 06 355 and EP-A 0 656 914. The end groups of the polyglyoxylic acids can have different structures.

Polyamidocarboxylic acids and modified polyamidocarboxylic acids suitable as component (B) are known, for example, from EP-A454 126, EP-B511 037, WO-A 94/01486 and EP-A 581 452.

As component (B) use is also made, in particular, of polyaspartic acids or of cocondensates of aspartic acid with other amino acids, $C_4$–$C_{25}$ mono- or dicarboxylic acids, and/or $C_4$–$C_{25}$ mono- or diamines. Particular preference is given to using polyaspartic acids which are prepared in phosphorus-containing acids and are modified with $C_6$–$C_{22}$ mono- or dicarboxylic acids and/or with $C_6$–$C_{22}$ mono- or diamines.

Condensation products of citric acid with hydroxycarboxylic acids or polyhydroxy compounds that are suitable as component (B) are known, for example, from WO 93/22362 and WO-A 92/16493. Such carboxyl-containing condensates usually have molar masses of up to 10,000, preferably up to 5000.

Also suitable as component (B) are ethylenediaminedisuccinic acid, oxydisuccinic acid, aminopolycarboxylates, aminopolyalkylenephosphonates and polyglutamates. In addition to component (B) it is also possible to use oxidized starches as organic cobuilders.

Surfactants

In addition to the compounds of the invention it is also possible to employ further surfactants.

Examples of suitable anionic surfactants (C) are fatty alcohol sulfates of fatty alcohols with 8 to 22, preferably 10 to 18, carbons, e.g. $C_9$ to $C_{11}$ alcohol sulfates, $C_{12}$ to $C_{14}$ alcohol sulfates, cetyl sulfate, myristyl sulfate, palmityl sulfate, stearyl sulfate and tallow fatty alcohol sulfate.

Other suitable anionic surfactants are sulfated, ethoxylated $C_8$ to $C_{22}$ alcohols (alkyl ether sulfates) and their soluble salts. Compounds of this type are prepared, for example, by initially alkoxylating a $C_8$ to $C_{22}$, preferably a $C_{10}$ to $C_{18}$, alcohol, for example a fatty alcohol, and then sulfating the alkoxylation product. Ethylene oxide is preferably used for the alkoxylation, in which case from 2 to 50 mol, preferably from 3 to 20 mol, of ethylene oxide are employed per mole of alcohol. However, the alcohols can also be alkoxylated using propylene oxide alone and, where appropriate, butylene oxide. Also suitable are those alkoxylated $C_8$ to $C_{22}$ alcohols which contain ethylene oxide and propylene oxide or ethylene oxide and butylene oxide or ethylene oxide and propylene oxide and butylene oxide. The alkoxylated $C_8$ to $C_{22}$ alcohols can contain the ethylene oxide, propylene oxide and butylene oxide units in the form of blocks or in random distribution. Depending on the nature of the alkoxylation catalyst, alkyl ether sulfates of broad or narrow alkylene oxide distribution can be obtained.

Further suitable anionic surfactants are alkanesulfonates, such as $C_8$- to $C_{24}$-, preferably $C_{10}$- to $C_{18}$-alkanesulfonates, and also soaps, for example the Na and K salts of $C_8$ to $C_{24}$ carboxylic acids.

Other suitable anionic surfactants are $C_9$ to $C_{20}$ linear alkylbenzenesulfonates (LAS) and $C_9$ to $C_{20}$ alkyltoluenesulfonates.

Also suitable as anionic surfactants (C) are $C_8$ to $C_{24}$ olefinsulfonates and -disulfonates, which may also constitute mixtures of alkene- and hydroxyalkanesulfonates and -disulfonates; alkyl ester sulfonates, sulfonated polycarboxylic acids, alkylglycerolsulfonates, fatty acid glycerol ester sulfonates, alkylphenyl polyglycol ether sulfates, paraffinsulfonates having from about 20 to about 50 C atoms (based on paraffin mixtures or paraffin obtained from natural sources), alkyl phosphates, acyl isethionates, acyl taurates, acyl methyltaurates, alkylsuccinic acids, alkenylsuccinic acids or their monoesters or monoamides, alkylsulfosuccinic acids or their amides, mono- and diesters of sulfosuccinic acids, acyl sarcosinates, sulfated alkyl polyglucosides, alkylpolyglycol carboxylates, and hydroxyalkyl sarcosinates.

The anionic surfactants are preferably added in the form of salts to the detergent. Suitable cations in these salts are ions of alkali metals such as sodium, potassium and lithium, and ammonium salts, for example hydroxyethylammonium, di(hydroxyethyl)ammonium and tri(hydroxyethyl) ammonium salts.

Component (C) is present in the novel textile detergent formulation in an amount of preferably from 3 to 30% by weight, in particular from 5 to 15% by weight. If $C_9$ to $C_{20}$ linear alkylbenzenesulfonates (LAS) are among the ingredients used, they are usually employed in an amount of up to 10% by weight, in particular up to 8% by weight. It is possible to employ only a single class of anionic surfactants, for example only fatty alcohol sulfates or only alkylbenzenesulfonates, although it is also possible to use mixtures of different classes, for example a mixture of fatty alcohol sulfates and alkylbenzenesulfonates. Within the individual classes of anionic surfactants it is also possible to employ mixtures of different species.

Examples of further suitable nonionic surfactants (D) are alkoxylated $C_8$ to $C_{22}$ alcohols, such as fatty alcohol alkoxylates or oxo alcohol alkoxylates. Alkoxylation can be carried out with ethylene oxide, propylene oxide and/or butylene oxide. Surfactants which can be employed in this context are all alkoxylated alcohols which contain at least two added-on molecules of an abovementioned alkylene oxide. Also suitable in this context are block polymers of ethylene oxide, propylene oxide and/or butylene oxide, or adducts which contain these alkylene oxides in random distribution. From 2 to 50, preferably from 3 to 20, mol of at least one alkylene oxide are used per mole of alcohol. Ethylene oxide is preferably employed as the alkylene oxide. The alcohols preferably have from 10 to 18 carbons. Depending on the nature of the alkoxylation catalyst, alkoxylates having a broad or narrow alkylene oxide distribution can be obtained.

Another class of suitable nonionic surfactants is that of alkylphenol alkoxylates, such as alkylphenol ethoxylates having $C_6$ to $C_{14}$ alkyl chains and from 5 to 30 mol of alkylene oxide units.

Another class of nonionic surfactants is that of alkyl polyglucosides or hydroxyalkyl polyglucosides having 8 to 22, preferably 10 to 18, carbons in the alkyl chain. These compounds usually contain from 1 to 20, preferably 1.1 to 5, glucoside units.

Another class of nonionic surfactants is that of N-alkylglucamides having $C_6$ to $C_{22}$ alkyl chains. Such compounds are obtained, for example, by acylating reductively aminated sugars with appropriate long-chain carboxylic acid derivatives.

Also possessing suitability as nonionic surfactants (D) are block copolymers of ethylene oxide, propylene oxide and/or butylene oxide (Pluronic and Tetronic grades from BASF), polyhydroxy- or polyalkoxy-fatty acid derivatives, such as polyhydroxy-fatty acid amides, N-alkoxy- or N-aryloxy-polyhydroxy-fatty acid amides, fatty acid amide ethoxylates, especially with those with capped end groups, and fatty acid alkanolamide alkoxylates.

Component (D) is present in the novel textile detergent formulation in an amount of preferably from 1 to 20% by weight, in particular from 3 to 12% by weight. It is possible to employ only one class of nonionic surfactants, especially only alkoxylated $C_8$ to $C_{22}$ alcohols, although it is also possible to use mixtures of different classes. Within the individual classes of nonionic surfactants, it is also possible to employ mixtures of different species.

Since the balance between the abovementioned classes of surfactant is important for the effectiveness of the novel detergent formulation, anionic surfactants (C) and nonionic surfactants (D) are preferably in a weight ratio of from 95:5 to 20:80, in particular from 70:30 to 50:50.

Furthermore, cationic surfactants (E) can also be present in the novel detergents.

Examples of suitable cationic surfactants are surface-active compounds containing ammonium groups, for example alkyldimethylammonium halides and compounds of the formula $RR'R''R'''N^+X^-$ where R to R''' are alkyl, aryl, alkylalkoxy, arylalkoxy, hydroxyalkyl(alkoxy) or hydroxyaryl(alkoxy) and X is an appropriate anion.

The novel detergents may if desired also contain ampholytic surfactants (F), examples being aliphatic derivatives of secondary or tertiary amines containing an anionic group in one of the side chains, alkyldimethylamine oxides, or alkyl- or alkoxymethylamine oxides.

Components (E) and (F) can be present in the detergent formulation in amounts of up to 25%, preferably 3–15%.

Bleaches

In a further preferred embodiment, the novel textile detergent formulation additionally contains from 0.5 to 30% by weight, especially from 5 to 27% by weight, in particular from 10 to 23% by weight, of bleaches (G). Examples are alkali perborates or alkali carbonate perhydrates, especially the sodium salts.

One example of an organic peracid which can be used is peracetic acid, which is preferably used in commercial textile washing or commercial cleaning.

Bleach or textile detergent compositions that can be used with advantage include $C_{1-12}$ percarboxylic acids, $C_{8-16}$ dipercarboxylic acids, imidopercaproic acids, or aryldipercaproic acids. Preferred examples of acids that can be used are peracetic acid, linear or branched octane-, nonane-, decane- or dodecanemonoperacids, decane and dodecanediperacid, mono- and diperphthalic acids, -isophthalic acids and -terephthalic acids, phthalimidopercaproic acid and terephthaloyldipercaproic acid. It is likewise possible to use polymeric peracids, for example those containing acrylic acid structural units in which there is a peroxy function. The percarboxylic acids can be used as free acids or as salts of the acids, preferably alkali metal salts or alkaline earth metal salts. These bleaches (G) are used alone or in combination with from 0 to 15% by weight, preferably from 0.1 to 15% by weight and, in particular, from 0.5 to 8% by weight of bleach activators (H). In the case of color detergents, the bleach (G) (if present) is generally employed without bleach activator (H); otherwise, customary bleach activators (H) are present as well.

Suitable bleach activators (H) are:

polyacylated sugars, for example pentaacetylglucose;

acyloxybenzenesulfonic acids and their alkali metal and alkaline earth metal salts, for example sodium p-isononanoyloxybenzenesulfonate or sodium p-benzoyloxybenzenesulfonate;

N,N-diacylated and N,N,N',N'-tetracylated amines, for example N,N,N',N'-tetracetyl-methylenediamine and -ethylenediamine (TAED), N,N-diacetylaniline, N,N-diacetyl-p-toluidine or 1,3-diacylated hydantoins, such as 1,3-diacetyl-5,5-dimethylhydantoin;

N-alkyl-N-sulfonylcarboxamides, for example N-methyl-N-mesylacetamide or N-methyl-N-mesylbenzamide;

N-acylated cyclic hydrazides, acylated triazoles or urazoles, for example monoacetyl-maleic hydrazide;

O,N,N-trisubstituted hydroxylamines, for example O-benzoyl-N,N-succinylhydroxylamine, O-acetyl-N,N-succinyl-hydroxylamine or O,N,N,-triacetylhydroxylamine;

N,N'-diacylsulfurylamides, for example N,N'-dimethyl-N,N'-diacetylsulfurylamide or N,N'-diethyl-N,N'-dipropionylsulfurylamide;

triacyl cyanurates, for example triacetyl cyanurate or tribenzoyl cyanurate;

carboxylic anhydrides, for example benzoic anhydride, m-chlorobenzoic anhydride or phthalic anhydride;

1,3-diacyl-4,5-diacyloxyimidazolines, for example 1,3-diacetyl-4,5-diacetoxyimidazoline;

tetraacetylglycoluril and tetrapropionylglycoluril;

diacylated 2,5-diketopiperazines, for example 1,4-diacetyl-2,5-diketopiperazine;

acylation products of propylenediurea and 2,2-dimethylpropylenediurea, for example tetraacetylpropylenediurea;

α-acyloxy-polyacyl-malonamides, for example α-acetoxy-N,N'-diacetylmalonamide;

diacyl-dioxohexahydro-1,3,5-triazines; for example 1,5-diacetyl-2,4-dioxohexahydro-1,3,5-triazine;

benz(4H)-1,3-oxazin-4-ones with alkyl radicals, for example methyl, or aromatic radicals, for example phenyl, in position 2.

The bleaching system described, comprising bleaches and bleach activators, may if desired also include bleaching catalysts. Examples of suitable bleaching catalysts are quatemized imines and sulfonimines, which are described in U.S. Pat. No. 5,360,569 and EP-A 0 453 003, for example. Particularly effective bleaching catalysts are manganese complexes, which are described for example in WO-A 94/21777. When used in the detergent formulations, such compounds are incorporated at most in amounts of up to 1.5% by weight, in particular up to 0.5% by weight.

In addition to the bleaching system described, comprising bleaches, bleach activators and possibly bleaching catalysts, the use of systems with enzymatic peroxide release, or of photoactivated bleaching systems, is also conceivable for the novel textile detergent formulation.

Enzymes

In another preferred embodiment, the novel textile detergent formulation additionally contains from 0.05 to 4% by weight of enzymes (J). Enzymes preferably employed in detergents are proteases, amylases, lipases and cellulases. The amounts of the formulated enzyme that are preferably added are from 0.1–1.5% by weight, with particular preference from 0.2 to 1.0% by weight. Examples of suitable proteases are Savinase and Esperase (producer: Novo Nordisk). A suitable lipase is, for example, Lipolase (producer: Novo Nordisk). An example of a suitable cellulase is Celluzym (producer: Novo Nordisk). Also possible is the use of peroxidases for activating the bleaching system. Individual enzymes or a combination of different enzymes can be employed. If desired, the novel textile detergent formulation may also comprise enzyme stabilizers, for example calcium propionate, sodium formate or boric acids or their salts, and/or antioxidants.

Further ingredients

In addition to the abovementioned principal components (A) to (J) the novel textile detergent formulation may also include the following additional customary additives in the amounts common for each:

graying inhibitors and soil release polymers

Examples of suitable soil release polymers and/or graying inhibitors for detergents are:

polyesters of polyethylene oxides with ethylene glycol and/or propylene glycol and aromatic dicarboxylic acids or aromatic and aliphatic dicarboxylic acids;

polyesters of polyethylene oxides, endgroup-capped at one end, with di- and/or polyhydric alcohols and dicarboxylic acid.

Polyesters of this kind are known, for example, from U.S. Pat. No. 3,557,039, GB-A 1 154 730, EP-A-1

85 427, EP-A-241 984, EP-A-241 985, EP-A-272 033 and U.S. Pat. No. 5,142,020.

Other suitable soil release polymers are amphiphilic graft polymers or copolymers of vinyl esters and/or acrylic esters on to polyalkylene oxides (cf. U.S. Pat. No. 4,746,456, U.S. Pat. No. 4,846,995, DE-A-37 11 299, U.S. Pat. No. 4,904,408, U.S. Pat. No. 4,846, 994 and U.S. Pat. No. 4,849,126), or modified celluloses, such as methylcellulose, hydroxypropylcellulose or carboxymethylcellulose, for example.

Color transfer inhibitors, for example homo- and copolymers of vinylpyrrolidone, of vinylimidazole, of vinyloxazolidone or of 4-vinylpyridine N-oxide with molar masses from 15,000 to 100,000, and also crosslinked, finely divided polymers based on these monomers;

nonsurfactant foam suppressants or foam inhibitors, for example organopolysiloxanes and mixtures thereof with microfine, possibly silanized silicic acid, and also paraffins, waxes, including microcrystalline waxes, and mixtures thereof with silanized silicic acid;

complexing agents (also in the function of organic cobuilders);

fluorescent whiteners;

polyethylene glycols; polypropylene glycols;

perfumes or fragrances;

fillers;

inorganic extenders, for example sodium sulfate;

formulation auxiliaries;

solubility improvers;

opacifying and pearlescence agents;

colorants;

corrosion inhibitors;

peroxide stabilizers;

electrolytes.

The novel detergent formulation is solid, i.e. is usually in powder or granule form or in the form of extrudates or tablets.

The novel pulverulent or granular detergents can include up to 60% by weight of inorganic extenders. Sodium sulfate is usually used for this purpose. Preferably, however, the extender content of the novel detergents is low and is only up to 20% by weight, with particular preference only up to 8% by weight, especially in the case of compact or ultra-compact detergents. The solid detergents according to the invention can have various bulk densities in the range from 300 to 1300 g/l, in particular from 550 to 1200 g/l. Modern compact detergents generally have high bulk densities and a granular composition. For the desired compaction of the detergent it is possible to employ the techniques customary in the art.

The detergent formulation of the invention is prepared and, if desired, packaged in accordance with customary methods.

The text below indicates typical compositions of compact heavy-duty detergents and color detergents (the percentages below and in the examples are by weight; the data in brackets in the case of compositions (a) and (b) are preferred ranges):

| (a) Composition of compact heavy-duty detergents (pulverulent or granular) | |
|---|---|
| 1–60% (8–30%) | of at least one anionic surfactant (C) and of a compound according to the invention, alone or in combination with a nonionic surfactant (D) |
| 5–50% (10–45%) | of at least one inorganic builder (A) |
| 0.1–20% (0.5–15%) | of at least one organic cobuilder (B) |
| 5–30% (10–25%) | of an inorganic bleach (G) |
| 0.1–15% (1–8%) | of a bleach activator (H) |
| 0–1% (max 0.5%) | of a bleaching catalyst |
| 0.05–5% (0.2–2.5%) | of a color transfer inhibitor |
| 0.3–1.5% | of a soil release polymer |
| 0.1–4% (0.2–2%) | of enzyme or enzyme mixture (J) |

Further customary additives:
  sodium sulfate, complexing agents, phosphonates, fluorescent whiteners, perfume oils, foam suppressants, graying inhibitors, bleach stabilizers.

| (b) Composition of color detergents (pulverulent or granular) | |
|---|---|
| 3–50% (8–30%) | of at least one anionic surfactant (C) and of a compound according to the invention, alone or in combination with a nonionic surfactant (D) |
| 10–60% (20–55%) | of at least one inorganic bleach (G) |
| 0–15% (0–5%) | of an inorganic bleach (G) |
| 0.05–5% (0.2–2.5%) | of a color transfer inhibitor |
| 0.1–20% (1–8%) | of at least one organic cobuilder (B) |
| 0.2–2% | of enzyme or enzyme mixture (J) |
| 0.2–1.5% | of a soil release polymer |

Further customary additives:
  sodium sulfate, complexing agents, phosphonates, fluorescent whiteners, perfume oils, foam suppressants, graying inhibitors, bleach stabilizers.

The invention is illustrated by the following examples.

PREPARATION EXAMPLES

Example 1

Reaction product of rapeseed oil with methylamine, and subsequent ethoxylation of the amide with 10 EO (ethyleneoxide units)

Amidation 435.0 g (0.5 mol) of rapeseed oil and 18.0 g of $NaOCH_3$ (30% strength in methanol, 0.1 mol) were charged to an autoclave and at room temperature 63 ml (1.55 mol) of methylamine were injected. The reaction solution was then heated to 120° C. and left at this temperature for two hours. It was cooled, the autoclave was let down, and then the product was transferred at 50° C. to a stirred apparatus, for phase separation. 250 ml of 2-butanone and 500 ml of water were added. The pH was adjusted to 3–4 with HCl. After phase separation was complete, two washing steps were conducted with 500 ml of water each time in order to remove final traces of glycerol and any amine present. The product was concentrated under reduced pressure and the residue was dried under the subatmospheric pressure produced by an oil pump. A viscous brown oil was obtained which was analyzed by IR and GC.

Ethoxylation 420.0 g (0.5 mol) of rapeseed oil N-methylamide and 18.0 g of $NaOCH_3$ (30% strength in methanol, 0.1 mol) were dried in an autoclave at 120° C./16 mbar for two hours. Then 220.0 g (5.0 mol) of ethylene oxide were fed in at a maximum pressure of 3.5 bar, still at 120° C. After the end of the reaction, the reaction mixture was cooled to 80° C. and devolatilized under reduced pressure until free from ethylene oxide. The resulting product was a viscous brown oil which was analyzed by GC. In addition, the OH number and polyethylene glycol content were determined.

OH number=75 mg of KOH/g
PEG=4.21%

Example 2

Reaction product of coconut oil with N-butylethanolamine and subsequent ethoxylation of the amide with 10 EO Amidation 90.8 g (0.775 mol) of N-butylethanolamine and 4.5 g of $NaOCH_3$ (30% strength in methanol, 0.025 mol) were heated to 80° C., and then 174.7 g (0.25 mol) of coconut oil were introduced dropwise over the course of 80 minutes. The batch was subsequently stirred for 15 minutes, after which the reaction was over (IR check). Then 250 ml of water were added, the heating was removed and the pH was adjusted to 3–4 with hydrochloric acid. After phase separation was complete, two washing operations were performed with 250 ml of water each time. The product was concentrated under reduced pressure and the residue was dried under the reduced pressure of an oil pump. A viscous brown oil was obtained.

Ethoxylation 225.0 g (0.23 mol) of coconut oil N-butylethanolamide and 4.5 g of $NaOCH_3$ (30% in methanol, 0.025 mol) were dried in an autoclave at 120° C./16 mbar for two hours. Then 100.0 g (2.3 mol) of ethylene oxide were fed in at a maximum pressure of 3.5 bar, still at 120° C. After the end of the reaction, the reaction mixture was cooled to 80° C. and devolatilized under reduced pressure until the product was free from ethylene oxide. The resulting product was a viscous brown oil which was analyzed by GC. In addition, the OH number and the content of polyethylene glycol were determined.

OH number=114 mg of KOH/g
PEG=2.94%

Example 3

Reaction product of rapeseed oil with N-methylethanolamine and subsequent ethoxylation of the amide with 6 EO Amidation 348.9 g (4.65 mol) of N-methylethanolamine and 27.0 g of $NaOCH_3$ (30% strength in methanol, 0.15 mol) were heated to 80° C., and then 1305.0 g (1.5 mol) of rapeseed oil were introduced dropwise over the course of 80 minutes. The batch was subsequently stirred for 15 minutes, after which the reaction was over (IR check). Then 1000 ml of water were added, the heating was removed and the pH was adjusted to 3–4 with hydrochloric acid. After phase separation was complete, two washing operations were performed with 750 ml of water each time. The product was concentrated under reduced pressure and the residue was dried under the reduced pressure of an oil pump. The product was a viscous brown oil.

Ethzoxylation 426.5 g (0.5 mol) of rapeseed oil N-methylethanolamide and 9.0 g of $NaOCH_3$ (30% strength in methanol, 0.05 mol) were dried in an autoclave at 120° C./16 mbar for two hours. Then 132.0 g (3.0 mol) of ethylene oxide were fed in at a maximum pressure of 3.5 bar, still at 120° C. After the end of the reaction, the reaction mixture was cooled to 80° C. and devolatilized under reduced pressure until the product was free from ethylene oxide. The product was a viscous brown oil which was analyzed by GC. In addition, the OH number and the content of polyethylene glycol were determined.

OH number=95 mg of KOH/g
PEG=3.3%

Example 4

Reaction product of rapeseed oil with N-methylethanolamine and subsequent ethoxylation of the amide with 7 EO Amidation Amidation was carried out as described in Example 3.

Ethoxylation

Ethoxylation was carried out as described in Example 3 but using 154 g (3.5 mol) of ethylene oxide. The product was a viscous brown oil which was analyzed by GC.

PERFORMANCE PROPERTIES

Performance properties of the fatty acid amide derivatives that were investigated were the pH, interfacial tension, surface tension and wetting power. The results measured for the substances of Examples 3 and 4 are compiled in Table 1 and compared with two samples from comparison examples.

The interfacial tension (IFT) was determined as a function of the contact time between aqueous surfactant solution and an oil phase.

The surface tension (SFT) was determined in accordance with DIN 53914 by measuring the force, in mN/m, required to lift a plate or a horizontally suspended ring from the surface of the liquid.

The wetting power was determined in accordance with DIN 53901.

TABLE 1

Test results: Rapeseed oil N-methylethanolamide + EO

| Sample | Compar. C1 | | Compar. C2 | | Example 3 | | Example 4 | |
|---|---|---|---|---|---|---|---|---|
| Consistency, each 100% | dark brown, liquid | | dark brown, liquid | | viscous, brown | | viscous, brown | |
| pH (g/l) | 9.2 | | 9.3 | | 9.7 | | 9.9 | |
| IFT [mN/m] (1 g/l; 25° C.) | 1 min | 30 min | 1 min | 30 min | 1 min | 30 min | 1 min | 30 min |
| Decane | 5.1 | 3.7 | 4.9 | 3.9 | 1.1 | 0.19 | 3.7 | 0.61 |
| Olive oil | 2.8 | 2.4 | 2.6 | 2.4 | 3.3 | 0.37 | 2.4 | 0.20 |
| Neutral oil 1A | 0.26 | 0.37 | 0.39 | 0.72 | 0.23 | 0.32 | 0.18 | 0.25 |

TABLE 1-continued

Test results: Rapeseed oil N-methylethanolamide + EO

| Sample | Compar. C1 | | Compar. C2 | | Example 3 | | Example 4 | |
|---|---|---|---|---|---|---|---|---|
| Hexadecane | 0.30 | 0.33 | 0.35 | 0.40 | 0.11 | 0.40 | 0.07 | 0.16 |
| SFT [mN/m] | 0.2 g/l | 1 g/l | 0.2 g/l | 1 g/l | 0.2 g/l | 1 g/l | 0.2 g/l | 1 g/l |
| 25° C. | 35.4 | 34.8 | 38.4 | 37.6 | 34.2 | 33.6 | 34.2 | 33.1 |
| 40° C. | 31.7 | 32.3 | 32.4 | 32.4 | 30.5 | 30.7 | 31.2 | 31.1 |
| Wetting power on cotton [s] (1 g/l; 23° C.) | 150 | | >300 | | 68 | | 102 | |

Compar. C1=Rapeseed oil N-methylethanolamide+6 EO, prepared by the method of Example 3, but removal of glycerol by dispersion with hot water and filtration in accordance with DE-A1-42 18 837.

Compar. C2=Rapeseed oil N-methylethanolamide+7 EO, prepared by the method of Example 4, but removal of glycerol by filtration in accordance with WO 96/18608.

From the results of Table 1, it is evident that the compounds according to the invention exhibit a substantially improved set of properties as nonionic surfactants relative to the comparison products. Particular emphasis is drawn to the low levels of surface tension, interfacial tension and wetting power.

WASHING EXPERIMENTS

The substances for Examples 3 and 4 were also tested under standard conditions (60° C., 5 g/l) in a model detergent formulation together with a $C_{13/15}$ oxo alcohol, reacted with 7 mol of ethylene oxide, as nonionic surfactant 2 (19% surfactant addition, of which 47% substance from Example 3 or 4 and 53% said nonionic surfactant). The comparison C3 used was an analogous model detergent formulation with 19% surfactant addition, comprising 47% of a $C_{12/18}$-alkyl sulfate as anionic surfactant and 53% of said nonionic surfactant.

The washing experiments were conducted under the following conditions:

| | |
|---|---|
| Washing machine | Launder O-meter from Atlas |
| Washing cycles | 1 |
| Rinse cycles | 1 |
| Washing temperature | 60° C. |
| Duration of wash | 30 min. |
| Water hardness | 3 mmol/l |
| Ca/Mg | 4:1 |
| Liquor volume | 250 ml |
| Detergent concentration | 5 g/l |
| Soiled fabric | WFK 10 D, WFK 20 D (soiled with skin grease/carbon black), test fabrics from WfK Testgewebe GmbH, Brüggen EMPA 101, EMPA 104 (soiled with oilve oil/carbon black), test fabrics from Eidgenössische Material-prüfungsanstalt, St. Gallen |
| Detergent formulation A: | |
| Zeolite A | 30% |
| Sodium carbonate | 12% |
| Sodium silicate | 3% |
| Tylose CR 1500 p | 1.2% |
| Sodium perborate monohydrate | 14.4% |
| Tetraacetylethylenediamine | 4% |
| Acrylic acid-maleic acid copolymer (MW 70,000) | 5% |
| Soap | 0.5% |
| Sodium sulfate | 4% |
| Water | 6.9% |
| Surfactant or surfactant mixture | 19% |

After rinsing, the load was spun and the fabrics hung up individually to dry. The fabric was measured, with 6 measurement points per piece of fabric, using an Elrepho 2000 from Data Color, Heidenheim. The reflectance was measured at 480 nm. Large values for the reflectance indicate good soil release and a high primary washing power.

Table 2 below compiles the sums of the measured reflectances for the individual fabrics, and the mean of the primary washing power (absolute effectiveness).

absolute effectiveness=100×[sum (R after wash)−(R before wash)]/
[sum (R before soiling)−sum(R before wash)]

TABLE 2

Primary washing power

| Surfactant 1 | Surfactant 2 | Reflectance | Absolute effectiveness |
|---|---|---|---|
| None | | 144.3 | 40.4 |
| Comparison C3 | no | 212.7 | 83.3 |
| Comparison C3 | yes | 181.4 | 61.9 |
| Example 3 | no | 234.0 | 89.1 |
| Example 3 | yes | 186.2 | 71.2 |
| Example 4 | no | 223.4 | 86.4 |
| Example 4 | yes | 199.8 | 78.1 |

From the results of Table 2 it is evident that the compounds according to the invention have a better primary washing power than the comparison solvents. The compounds according to the invention are highly suitable for use in detergent and cleaning formulations.

We claim:

1. A process for preparing an alkoxylated amide of the formula (I):

$$R^1-CO-NR^2-CHR^3-CHR^4-O-(CHR^5-CHR^6-O)_n-H \quad (I)$$

wherein $R^1$ is a linear or branched aliphatic $C_{5-25}$ radical containing 0–5 double bonds, $R^2$ is hydrogen or a linear or branched $C_{1-20}$ alkyl which may be interrupted by from 1 to 5 oxygens, $R^3$, $R^4$, $R^5$ and $R^6$ are hydrogen, or not more than one of $R^3$ and $R^4$ and not more than one of $R^5$ and $R^6$ are methyl or ethyl, and n is 1–100, comprising:

(1) reacting a glyceride of a fatty acid of the formula (II):

$$R^1\text{—COOH} \qquad (II)$$

wherein $R^1$ is as defined above,
with an amine of the formula (III):

$$HNR^2R^7 \qquad (III)$$

wherein $R^7$ is hydrogen or —$CHR^3$—$CHR^4$—OH, in which not more than one of $R^2$ and $R^7$ is hydrogen, to produce an amide of the formula (IV):

$$R^1\text{—CO—}NR^2\text{—}R^7 \qquad (IV)$$

wherein $R^1$, $R^2$ and $R^7$ are as defined above, and glycerol, (2) adding an aqueous acid solution to the reaction mixture from (1) until the reaction mixture has a pH from 1 to 7, in order to bring about phase separation into a glycerol-containing aqueous phase and an organic phase containing the amide of the formula (IV), followed by separating off the aqueous phase, thereby separating off the glycerol, and then (3) reacting the amide of the formula (IV) with ethylene oxide, propylene oxide and/or butylene oxide to produce the alkoxylated amide of the formula (I).

2. A process as claimed in claim 1, where $R^1$ derives from a natural fatty acid.

3. The process as claimed in claim 1, wherein $R^3$, $R^4$, $R^5$ and $R^6$ are hydrogen.

4. The process as claimed in claim 1, wherein one of $R^3$ and $R^4$ are methyl or ethyl, and the other of $R^3$ and $R^4$ is hydrogen.

5. The process as claimed in claim 1, wherein one of $R^5$ and $R^6$ are methyl or ethyl, and the other of $R^5$ and $R^6$ is hydrogen.

6. The process as claimed in claim 1, wherein
one of $R^3$ and $R^4$ are methyl or ethyl, and the other of $R^3$ and $R^4$ is hydrogen, and
one of $R^5$ and $R^6$ are methyl or ethyl, and the other of $R^5$ and $R^6$ is hydrogen.

7. A process for preparing fatty acid amides, comprising:

(1) reacting a fatty acid glyceride with an amine, to produce a fatty acid amide and glycerol, and (2) adding an aqueous acid solution to the reaction mixture from (1) to adjust the pH of the reaction mixture to a value from 1 to 7, thereby causing the reaction mixture to undergo phase separation into an aqueous phase comprising glycerol and an organic phase comprising the fatty acid amide, followed by separating off the aqueous phase.

8. A process for separating glycerol from a reaction mixture comprising glycerol and fatty acid amides, comprising:

adding an aqueous acid solution to the reaction mixture to adjust the pH of the reaction mixture to a value from 1 to 7, thereby causing the reaction mixture to undergo phase separation into an aqueous phase comprising glycerol and an organic phase comprising fatty acid amides, followed by separating off the aqueous phase.

9. The process as claimed in claim 8, wherein the reaction mixture originates from the reaction of fatty acid glycerides with amines.

10. A process for preparing fatty acid amides by reacting fatty acid glycerides with amines, wherein the reaction mixture obtained after the reaction is treated as claimed in claim 8.

11. The process as claimed in claim 8, wherein the reaction is carried out in the presence of a basic catalyst.

12. The process as claimed in claim 8, wherein the fatty acid radical in the fatty acid glyceride is a radical $R^1$—CO—, where $R^1$ is a linear or branched aliphatic $C_{5-25}$ radical containing from 0 to 5 double bonds.

13. The process as claimed claim 8, wherein the amine radical in the fatty acid amide is derived from ethanolamine, an N-alkylamine or N-alkylethanolamine with a linear or branched $C_{1-20}$-alkyl which may be interrupted by from 1 to 5 oxygen atoms, the ethanol radical optionally substituted by methyl or ethyl.

* * * * *